United States Patent [19]

Haber

[11] Patent Number: 4,749,712

[45] Date of Patent: Jun. 7, 1988

[54] ANTIINFLAMMATORY AND/OR ANALGESIC 5-ALKYLTHIOPHENES

[75] Inventor: Stephen B. Haber, Wilmington, Del.

[73] Assignee: E. I. Du Pont de Nemours and Company, Wilmington, Del.

[21] Appl. No.: 678,680

[22] Filed: Dec. 5, 1984

Related U.S. Application Data

[63] Continuation of Ser. No. 471,202, Mar., 1983, abandoned.

[51] Int. Cl.⁴ .................. A61K 31/38; C07D 401/00; C07D 333/12

[52] U.S. Cl. .................................. 514/438; 514/333; 514/336; 546/256; 546/284; 549/74; 549/75; 549/78; 549/80

[58] Field of Search ............... 424/263, 275; 546/256, 546/284; 549/74, 75, 78, 80; 514/438, 333, 336

[56] References Cited

U.S. PATENT DOCUMENTS

| | | | |
|---|---|---|---|
| 3,709,906 | 1/1973 | Yoshida | 549/75 |
| 3,901,908 | 8/1975 | Fitzi | 549/75 |
| 4,302,461 | 11/1981 | Cherkofsky | 549/75 |

*Primary Examiner*—Alan Siegel

[57] ABSTRACT

5-Alkyl-2,3-diarylthiophenes, such as 5-(1,1-dimethylethyl)-2,3-bis(4-methoxyphenyl)thiophene, 5-(1-methylpropyl)-2,3-bis(4-methoxyphenyl)thiophene and 5-cyclohexyl-2,3-bis(4-methoxyphenyl)thiophene, are useful in the treatment of inflammation and/or pain.

21 Claims, No Drawings

ANTIINFLAMMATORY AND/OR ANALGESIC 5-ALKYLTHIOPHENES

BACKGROUND OF THE INVENTION

1. Field of the Invention

This invention relates to 5-alkylthiophenes, pharmaceutical compositions containing them, and methods of using them to treat inflammation and/or pain in mammals. More particularly this invention relates to antiinflammatory and/or analgesic 5-alkyl-2,3-diarylthiophenes.

2. Prior Art

There is a continuing need for safe and effective antiinflammatory agents to treat inflammation, a disease process characterized by redness, fever, swelling, and pain. Arthritis, in its various forms, is the most prevalent, chronic, and severe of the inflammatory diseases. Traumatic injury and infection also involve inflammation, and antiinflammatory drugs are often used in their treatment as well.

The usefulness of many commercial antiinflammatories, however, is limited because of toxicity and adverse side-effects. Many produce gastric irritation and can cause changes in blood cells or can affect the central nervous system. Adreno-cortical steroids, for example, produce gastric irritation and suppression of normal adrenal function.

The present invention results from efforts to develop new anti-arthritic compounds with good antiinflammatory activity and minimal side effects that could be more effective in treating arthritis than are presently available drugs. In addition to antiinflammatory properties, some compounds of this invention have demonstrated analgesic activity in a test procedure. This additional property is desirable in treatment of arthritis or related diseases; however, such compounds can be employed solely to alleviate pain.

U.S. Pat. No. 3,707,475, (to Pfizer) discloses 2-alkyl-4,5-diarylimidazoles and their use as antiinflammatories. U.S. Pat. No. 3,709,906 (to Sankyo) discloses 2-alkyl-4,5-diarylpyrroles and their use as antiinflammatories. U.S. Pat. Nos. 3,901,908 and 3,929,807 (to Ciba Geigy) disclose 2-alkyl and 2-cycloalkyl-4,5-diarylimidazoles and their use as antiinflammatories. U.S. Pat. Nos. 4,021,553 and 4,190,725 (to Eli Lilly) disclose 5,6-diaryl-3-alkyl-1,2,4-triazines and their use as topical antiinflammatories. Rynbrandt et al., *J. Med. Chem.*, 24, 1507 (1981) disclose 2-alkyl-4,5-diarylthiazoles and their use as platelet aggregation inhibitors.

A number of references including J. L. Melles and H. J. Becker, *Rec. Trav. Chim.*, 72, 314 (1953) and S. Hauptmann and E. M. Werner, *J. Prakt. Chem.*, 314, 499 (1972) describe the preparation of 2,3-diarylthiophenes.

Antiinflammatory and/or analgesic 2,3-diarylthiophenes are described in U.S. Pat. No. 4,302,461, and coassigned U.S. Ser. No. 316,661, filed Nov. 2, 1981, in the name of S. B. Haber, U.S. Ser. No. 295,781, filed Aug. 27, 1981, in the name of S. B. Haber, U.S. Ser. No. 354,300, filed Mar. 3, 1982, in the name of S. B. Haber, and U.S. Ser. No. 354,643, filed Mar. 4, 1982, in the name of S. B. Haber. None has an alkyl substituent at the 5-position.

G. N. Schrauzer and V. P. Mayweg, *J. Am. Chem. Soc.*, 87, 1483–9 (1965) report 2,3-dimethyl-4,5-diphenylthiophene. No biological activity is disclosed.

R. E. Atkinson and F. E. Hardy, *J. Chem. Soc. Perkin II*, 27–30 (1972) report 5,5'-dimethyl-3-(2-benzimidazolyl)-2,2'-bithienyl and the 3-(2-indolyl) derivative, prepared in the course of fluorescence studies.

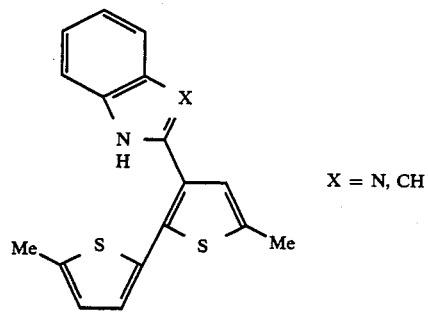

SUMMARY OF THE INVENTION

According to the present invention there is provided a compound having the formula:

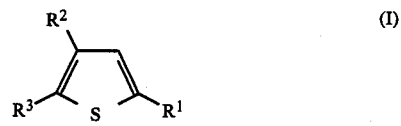

wherein $R^1$ is $C_1$–$C_6$ alkyl or $C_3$–$C_6$ cycloalkyl;

$R^2$ and $R^3$ are independently pyridyl or

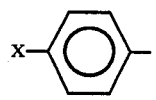

where X is H, F, Cl, Br, $NO_2$, $R^4$, $OR^4$, $R^4S(O)_n$, or $R^4R^5N$;

$R^4$ and $R^5$ are $CH_3$ or $C_2H_5$; and n is 0, 1 or 2; or a pharmaceutically suitable salt thereof.

There is also provided pharmaceutical compositions containing at least one of the aforesaid compounds and methods of using them to treat inflammation and/or pain in mammals.

PREFERRED SCOPE

Preferred are compounds of Formula I where:

$R^2$ and $R^3$ are independently

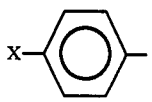

where X is $R^4$, $OR^4$, $R^4S$ or $R^4R^5N$; and where $R^4$ and $R^5$ are $CH_3$ or $C_2H_5$.

More preferred compounds are preferred compounds where X is $OR^4$.

Most preferred are compounds of Formula I where:

$R^2$ and $R^3$ are independently

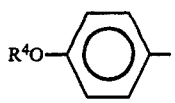

where $R^4$ is $CH_3$ or $C_2H_5$; and the carbon atom in $R^1$ which is α to the thiophene ring is tertiary or quaternary.

Compounds specifically preferred because of their biological activity are:

(a) 5-(1,1-dimethylethyl)-2,3-bis(4-methoxyphenyl)thiophene;
(b) 5-(1-methylpropyl)-2,3-bis(4-methoxyphenyl)thiophene; and
(c) 5-cyclohexyl-2,3-bis(4-methoxyphenyl)thiophene.

PHARMACEUTICAL SALTS

Included in this invention are pharmaceutically suitable salts of compounds of Formula I in which at least one of $R^2$ and $R^3$ is pyridyl or 4—($R^4R^5N$)phenyl. The preparation of such salts, which include salts with mineral acids such as hydrochloric, sulfuric, and nitric acids, is well known to those skilled in pharmaceuticals.

SYNTHESIS

A variety of procedures for the introduction of an alkyl group onto an aromatic nucleus are known and these may be used to convert 2,3-diarylthiophenes (II) to compounds of Formula I. Procedures that are particularly useful for the preparation of the compounds of the invention are illustrated below and in the examples.

The preparation of 2,3-diarylthiophenes (II) is described in Melles and Becker and Hauptmann and Werner, cited above.

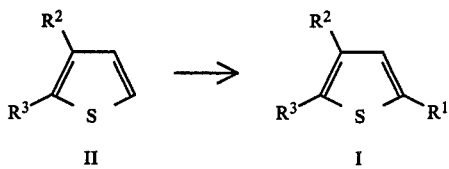

Method A

A 2,3-diarylthiophene II is treated with a strong base such as n-butyl lithium or t-butyl lithium in an aprotic solvent such as tetrahydrofuran, toluene or diethyl ether and then treated with alkylating agent such as methyl iodide to give a compound of Formula I. The reaction can be carried out at temperatures from about −78° to about 110° C.

Method B

Following the procedure of T. Sotoyama et al., *Bull. Chem. Soc. Jpn.*, 52, 1865 (1979) a 2,3-diarylthiophene II is metallated as in Method A and treated with a trialkylborane and then with iodine or bromine. Isolation of the 5-alkylthiophene product (I) is facilitated by removing the residual organoborane via an alkaline hydrogen peroxide oxidation, but this step is not necessary for the success of this reaction.

Method C

A 2,3-diarylthiophene (II) is metallated as in Method A and then treated with an alkyl ketone or aldehyde or cyclic alkanone. The resultant alcohol is then reduced to give a compound of Formula I. This reduction may be done with a reagent such as triethylsilane in the presence of an acid or with hydrogen in the presence of a catalyst such as palladium or platinum on an inert support.

Method D

A 2,3-diarylthiophene (II) in a solvent such as trichloroethylene, carbon disulfide or nitromethane is treated with a carbonium ion precursor such as isobutylene, t-butanol or 2,6-di-t-butylcresol in the presence of an acid catalyst such as aluminum chloride to give a compound of Formula I.

Compounds of Formula I in which either the radical $R^1$ is asymmetric and/or in which at least one of $R^2$ and $R^3$ is 4-methylsulfinylphenyl exist as mixtures of enantiomers or diastereoisomers. This invention includes such mixtures as well as preparations enriched in, or consisting substantially of, one or more of the components of the mixture.

The compounds of this invention and their synthesis are further illustrated by the following examples. All temperatures are in degrees centigrade.

EXAMPLE 1

5-Methyl-2,3-bis(4-methoxyphenyl)thiophene

A solution of 2,3-bis(4-methoxyphenyl)thiophene (4.4 g, 15 mmole) in 100 ml of toluene was dried by distilling off 75 ml of toluene. The solution was diluted with 150 ml of diethyl ether, cooled to 0°, and treated dropwise with 1.6M n-butyl lithium (13.5 ml, 1.4 equiv.). The reaction mixture was heated at reflux for 1.5 hours, cooled to 5°, treated with a solution of methyl iodide (2 ml, 2.1 equiv.) in 10 ml of diethyl ether, and then heated at reflux for an additional 2.5 hours. The cooled reaction mixture was poured into water and extracted with ethyl acetate. The organic extracts were washed with 1N HCl and brine, dried, and concentrated in vacuo. Recrystallization from ethanol provided the title compound (3 g, 64%), m.p. 93°–97°. Proton nuclear magnetic resonance (NMR) was consistent with the assigned structure.

EXAMPLE 2

5-(1-Methylpropyl)-2,3-bis(4-methoxyphenyl)thiophene

A solution of 2,3-bis(4-methoxyphenyl)thiophene (5.92 g, 20 mmole) in toluene (40 ml)/diethyl ether (130 ml) was treated with 1.6M n-butyl lithium (14 ml, 1.1 equiv.) and heated at reflux for 1.5 hours. The reaction mixture was cooled to −76° and treated dropwise with 1M tri-s-butylboron (22 ml, 1.1 equiv.). After 0.5 hours at −76°, the reaction mixture was stirred at 0° for 0.5 hours, recooled to −76° and treated with bromine (1 ml, 20 mmole) in 20 ml diethyl ether. The mixture was allowed to warm to room temperature, and then after 2 hours was treated sequentially with 50% (w/w) sodium hydroxide (2.3 ml) and 30% hydrogen peroxide (8 ml). The mixture was stirred overnight, and then extracted with ethyl acetate. The organic extracts were washed with water and brine, dried and concentrated in vacuo. Chromatography on a Waters Prep 500 (hexane/ethyl acetate, 9:1) provided the title compound (2.9 g, 41%) as an oil. Proton NMR was consistent with the assigned structure. Mass Spec. (MS): m/z 352 (M+), 323 (M—$C_2H_5$).

EXAMPLE 3

5-Cyclohexyl-2,3-bis(4-methoxyphenyl)thiophene a. 1-[4,5-bis(4-Methoxyphenyl)thien-2-yl]cyclohexanol A solution of 2,3-bis(4-methoxyphenyl)thiophene (5.92 g, 20 mmole) in toluene (20 ml)/diethyl ether (120 ml) was treated with 1.6M n-butyl lithium (14 ml, 1.1 equiv.) and heated at reflux for 1.5 hours. The reaction mixture was cooled to 0° and treated with a solution of cyclohexanone (2.3 ml, 1.1 equiv.) in 5 ml of diethyl ether. The mixture was stirred for 1.5 hours at 0° and 1 hour at room temperature, quenched with water, and extracted with ethyl acetate. The organic extracts were washed with brine, dried and concentrated in vacuo. Chromatography on a Waters Prep 500 (hexane/ethyl acetate, 3:1) provided the title compound (5.8 g, 74%) as an oil.

b. 5-Cyclohexyl-2,3-bis(4-methoxyphenyl)thiophene

A solution of 1-[4,5-bis(4-methoxyphenyl)thien-2-yl]cyclohexanol (5.8 g, 14.7 mmole) in 125 ml of methylene chloride at 0° was treated sequentially with triethylsilane (4.7 ml, 2 equiv.) and trifluoroacetic acid (1.3 ml, 1.14 equiv.). The reaction mixture was stirred for 40 minutes at 0° and for 2 hours at room temperature, and then partitioned between methylene chloride and water. The organic phase was washed with saturated aqueous sodium bicarbonate and brine, dried and concentrated in vacuo. Recrystallization from ethanol provided the title compound (3.9 g, 70%), m.p. 95°–98°. Proton NMR and infrared (IR) spectra were consistent with the assigned structure. MS: m/z 378 (M+).

EXAMPLE 4

5-(1,1-Dimethylethyl)-2,3-bis(4-methoxyphenyl)thiophene

A suspension of 2,3-bis(4-methoxyphenyl)thiophene (3.6 g, 12 mmole) and 2,6-di-t-butylcresol (2.4 g, 10.9 mmole) in 37 ml of nitromethane was cooled in an ice-/acetone bath and treated with a solution of aluminum chloride (1.8 g, 13.5 mmole) in 27 ml of nitromethane. The reaction mixture was stirred for 4 hours in the cooling bath and then left in the refrigerator ($\nu$0°) overnight. The mixture was poured into ice/water and extracted with ethyl acetate. The organic extracts were washed with 3N HCl, 1N sodium hydroxide and brine, dried and concentrated in vacuo. The material thereby obtained was combined with material from a similar reaction and chromatographed on a Waters Prep 500 (hexane/ethyl acetate, 9:1). Recrystallization from hexane provided the title compound (2.1 g, 29%), m.p. 112°–115°. Proton NMR and IR spectra were consistent with the assigned structure. MS: m/z 352 (M+), 337 (M—CH$_3$).

Anal. Calcd. for C$_{22}$H$_{24}$O$_2$S: C, 74.96; H, 6.86. Found: C, 74.7; H, 6.9.

The compounds of Examples 1–4 and other compounds which can be prepared by the procedures described above are shown in Table I.

TABLE I

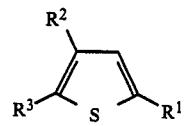

| Ex. No. | R$^1$ | R$^2$ | R$^3$ | m.p. (°C.) |
|---|---|---|---|---|
| 1 | CH$_3$ | 4-CH$_3$OC$_6$H$_4$ | 4-CH$_3$OC$_6$H$_4$ | 93–97° |
| 2 | CH(CH$_3$)(C$_2$H$_5$) | 4-CH$_3$OC$_6$H$_4$ | 4-CH$_3$OC$_6$H$_4$ | oil |
| 3 | c-C$_6$H$_{11}$ | 4-CH$_3$OC$_6$H$_4$ | 4-CH$_3$OC$_6$H$_4$ | 95–98° |
| 4 | C(CH$_3$)$_3$ | 4-CH$_3$OC$_6$H$_4$ | 4-CH$_3$OC$_6$H$_4$ | 112–115° |
| 5 | c-C$_3$H$_5$ | 4-CH$_3$OC$_6$H$_4$ | 4-CH$_3$OC$_6$H$_4$ | |
| 6 | n-C$_6$H$_{13}$ | 4-CH$_3$OC$_6$H$_4$ | 4-CH$_3$OC$_6$H$_4$ | |
| 7 | c-C$_6$H$_{11}$ | 4-FC$_6$H$_4$ | 4-FC$_6$H$_4$ | |
| 8 | C(CH$_3$)$_3$ | 4-CH$_3$C$_6$H$_4$ | 4-CH$_3$C$_6$H$_4$ | |
| 9 | c-C$_5$H$_9$ | 4-FC$_6$H$_4$ | 4-CH$_3$SC$_6$H$_4$ | |
| 10 | CH(CH$_3$)(C$_2$H$_5$) | 4-FC$_6$H$_4$ | 4-CH$_3$SO$_2$C$_6$H$_4$ | |
| 11 | CH(C$_2$H$_5$)(C$_3$H$_7$) | 4-FC$_6$H$_4$ | 4-ET$_2$NC$_6$H$_4$ | |
| 12 | c-C$_3$H$_5$ | 4-FC$_6$H$_4$ | 4-CH$_3$SOC$_6$H$_4$ | |
| 13 | c-C$_4$H$_7$ | 4-FC$_6$H$_4$ | 4-BrC$_6$H$_4$ | |
| 14 | C(CH$_3$)$_2$C$_3$H$_7$ | 4-FC$_6$H$_4$ | 4-ClC$_6$H$_4$ | |
| 15 | C(CH$_3$)$_3$ | 2-pyridyl | 4-EtOC$_6$H$_4$ | |
| 16 | C(C$_2$H$_5$)$_2$CH$_3$ | 3-pyridyl | C$_6$H$_5$ | |
| 17 | —C(cyclopentyl)—CH$_3$ | 4-pyridyl | 4-EtC$_6$H$_4$ | |
| 18 | C(CH$_3$)$_3$ | 4-NO$_2$C$_6$H$_4$ | 4-NO$_2$C$_6$H$_4$ | |

Et = C$_2$H$_5$

Dosage Forms

The antiinflammatory and/or analgesic agents of this invention can be administered to treat inflammation and/or relieve pain by any means that produces contact of the active agent with the agent's site of action in the body of a mammal. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.1 to 100 milligrams per kilogram of body weight. Ordinarily 0.5 to 50, and preferably 1 to 25 milligrams per kilogram per day given in divided doses 1 to 6 times a day or in sustained release form is effective to obtain desired results.

Dosage forms (compositions) suitable for internal administration contain from about 1 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions, it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Some of the compounds of this invention form salts. Solutions for parenteral administration of these compounds contain preferably a water soluble salt of the active ingredient, suitable stabilizing agents, and if necessary, buffer substances. Antioxidizing agents such as sodium bisulfite, sodium sulfite, or ascorbic acid either alone or combined are suitable statilizing agents. Also used are citric acid and its salts and sodium EDTA. In addition parenteral solutions can contain preservatives, such as benzalkonium chloride, methyl- or propyl-paraben, and chlorobutanol.

Suitable pharmaceutical carriers are described in *Remington's Pharmaceutical Sciences*, A. Osol, a standard reference text in this field.

Useful pharmaceutical dosage forms for administration of the compounds of this invention can be illustrated as follows:

CAPSULES

A large number of unit capsules are prepared by filling standard two-piece hard gelatin capsules each with 75 milligrams of powdered active ingredient, 150 milligrams of lactose, 24 milligrams of talc, and 6 milligrams magnesium stearate.

SOFT GELATIN CAPSULES

A mixture of active ingredient in soybean oil is prepared and injected by means of a positive displacement pump into gelatin to form soft gelatin capsules containing 75 milligrams of the active ingredient. The capsules are washed and dried.

TABLETS

A large number of tablets are prepared by conventional procedures so that the dosage unit is 75 milligrams of active ingredient, 6 milligrams of magnesium stearate, 70 milligrams of microcrystalline cellulose, 11 milligrams of cornstarch and 200 milligrams of lactose. Appropriate coatings may be applied to increase palatability or delay absorption.

INJECTABLE

A parenteral composition suitable for administration by injection is prepared by stirring 1.5% by weight of active ingredient in 10% by volume propylene glycol and water. The solution is sterilized by commonly used techniques.

SUSPENSION

An aqueous suspension is prepared for oral administration so that each 5 milliliters contain 25 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

INJECTABLE

A parenteral composition suitable for administration by injection is prepared by dissolving 1% by weight of active ingredient in sodium chloride injection U.S.P. XX and adjusting the pH of the solution to between 6 and 7. The solution is sterilized by commonly used techniques.

Use

To detect and compare the antiinflammatory activities of compounds in this series and standard drugs, a test was used based on a standard model of arthritis for which there is good correlation with human efficacy. The model is adjuvant-induced arthritis in rats. *Federation Proceedings*, 32 (2) (1973) "Models Used for the Study and Therapy of Rheumatoid Arthritis"—Symposium of the American Society for Pharmacology and Experimental Therapeutics—states "The rat polyarthritis produced by intradermal injection of a suspension of *Mycobacterium tuberculosis* in mineral oil (adjuvant) has been used extensively for the screening of drugs of potential use in rheumatoid arthritis."

Established Adjuvant-Induced Arthritis in Rats

Male Charles River Lewis rats (130–150 grams) are injected subcutaneously in the plantar area of the right hind paw with 0.1 ml of adjuvant (Difco heat-killed, lyophilized *Mycobacterium butyricum* suspended in mineral oil 5 mg/ml). 20 Non-arthritic controls are injected with mineral oil. The animals are held for 2 weeks to allow development of arthritis. Paw volumes (uninjected, left hind paw) are measured and the adjuvant-injected rats are culled and distributed to treatment groups of 10 of equal disease severity. Non-arthritic controls are distributed to 2 groups of 10. The rats are given oral doses of compound or PVA-Acacia (Polyvinyl Alcohol 1%, Gum acacia, U.S.P. 5%, Methylparaben 0.5%) (10 ml/kg) by gavage on that day and on the 6 following days. One day after the last dose the paw volumes (uninjected, left hind paw) are measured using a Ugo Basile Volume Differential Meter Model 7101.

$$\frac{\text{Arthritic Control Mean Paw Volume (ml)} - \text{Treatment Group Mean Paw Volume (ml)}}{\text{Arthritic Control Mean Paw Volume (ml)} - \text{Non-Arthritic Control Mean Paw Volume (ml)}} \times 100 =$$

% Decrease from Control Mean Paw Volume.

Dose-response regression lines of the percent decrease are plotted on semi-log paper by visual fit and the effective dose for 50% decrease from control paw volume (ED50) is determined by inspection. Data for some of the compounds of this invention are summarized in Table II.

Compounds from this series were also compared to indomethacin, phenylbutazone, ibuprofen, and aspirin.

Phenylquinone Writhing Test

A standard procedure for detecting and comparing the analgesic activity of compounds in this series for which there is a good correlation with human efficacy is the standard phenylquinone writhing test modified from Siegmund, et al., *Proc. Soc. Exp. Biol. Med.*, 95, 729 (1957). A test compound suspended in 1% methylcellulose was given orally to fasted (17-21 hours) female white mice, 5-20 animals per double blind test. Aqueous (0.01% phenyl-p-benzoquinone) phenylquinone, 0.20 ml per mouse, was injected intraperitoneally 6 minutes before observations were begun. At an appropriate time after the oral administration of the test compound, the mice were observed for 10 minutes for a characteristic stretching or writhing syndrome which is indicative of pain induced by phenylquinone. The effective analgesic dose for 50% of the mice ($ED_{50}$) was calculated by the moving average method of Thompson, W. R., *Bact. Rev.*, 11, 115-145 (1947); the time of peak activity was determined for many of the compounds. Data for some of the compounds are summarized in Table II together with data for some standard analgetic-antiinflammatory drugs.

TABLE II

| | Biological Activity | |
|---|---|---|
| Example | Adjuvant Arthritis $ED_{50}$ (mg/kg) | Phenylquinone Writhing (PQW) $ED_{50}$ (mg/kg) |
| 1 | 60 | 78 |
| 2 | 29 | 5.5 |
| 3 | (34% at 45)* | 47 |
| 4 | 36 | 1.4 |
| Indomethacin | 0.3 | 0.35 |
| Phenylbutazone | 10 | 80 |
| Ibuprofen | 100 | 10 |
| Aspirin | 305 | 135 |

*Value in parentheses indicates the percent reduction in paw volume at the indicated dose.

"Consisting essentially of" in the present disclosure is intended to have its customary meaning: namely, that all specified material and conditions are very important in practicing the invention but that unspecified materials and conditions are not excluded so long as they do not prevent the benefits of the invention from being realized.

What is claimed is:

1. A compound having the formula:

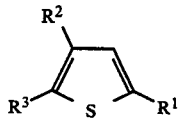
(I)

wherein
$R^1$ is $C_3$-$C_6$ alkyl or $C_3$-$C_6$ cycloalkyl, and the carbon atom which is α to the thiophene ring is tertiary or quaternary;
$R^2$ and $R^3$ are independently pyridyl or

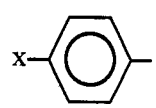

where X is H, F, Cl, Br, $NO_2$, $R^4$, $OR^4$, $R^4S(O)_n$, or $R^4R^5N$;
$R^4$ and $R^5$ are $CH_3$ or $C_2H_5$; and
n is 0, 1 or 2; or
a pharmaceutically suitable salt thereof.

2. A compound of claim 1 wherein:
$R^2$ and $R^3$ are independently

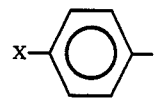

where X is $R^4$, $OR^4$, $R^4S$ or $R^4R^5N$; and
where $R^4$ and $R^5$ are $CH_3$ or $C_2H_5$.

3. A compound of claim 2 wherein X is $OR^4$.

4. A compound of claim 1 wherein:
$R^2$ and $R^3$ are independently

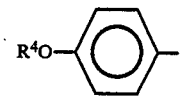

where $R^4$ is $CH_3$ or $C_2H_5$.

5. The compound of claim 1 which is 5-(1,1-dimethylethyl)-2,3-bis(4-methoxyphenyl)thiophene.

6. The compound of claim 1 which is 5-(1-methylpropyl)-2,3-bis(4-methoxyphenyl)thiophene.

7. The compound of claim 1 which is 5-cyclohexyl-2,3-bis(4-methoxyphenyl)thiophene.

8. A pharmaceutical composition consisting essentially of a suitable pharmaceutical carrier and an effective antiinflammatory or analgesic amount of a compound of claim 1.

9. A pharmaceutical composition consisting essentially of a suitable pharmaceutical carrier and an effective antiinflammatory or analgesic amount of a compound of claim 2.

10. A pharmaceutical composition consisting essentially of a suitable pharmaceutical carrier and an effective antiinflammatory or analgesic amount of a compound of claim 3.

11. A pharmaceutical composition consisting essentially of a suitable pharmaceutical carrier and an effective antiinflammatory or analgesic amount of a compound of claim 4.

12. A pharmaceutical composition consisting essentially of a suitable pharmaceutical carrier and an effective antiinflammatory or analgesic amount of a compound of claim 5.

13. A pharmaceutical composition consisting essentially of a suitable pharmaceutical carrier and an effective antiinflammatory or analgesic amount of a compound of claim 6.

14. A pharmaceutical composition consisting essentially of a suitable pharmaceutical carrier and an effective antiinflammatory or analgesic amount of a compound of claim 7.

15. A method of treating inflammation, pain or both in a mammal which comprises administering to the mammal an effective antiinflammatory or analgesic amount of a compound of claim 1.

16. A method of treating inflammation, pain or both in a mammal which comprises administering to the mammal an effective antiinflammatory or analgesic amount of a compound of claim 2.

17. A method of treating inflammation, pain or both in a mammal which comprises administering to the mammal an effective antiinflammatory or analgesic amount of a compound of claim 3.

18. A method of treating inflammation, pain or both in a mammal which comprises administering to the mammal an effective antiinflammatory or analgesic amount of a compound of claim 4.

19. A method of treating inflammation, pain or both in a mammal which comprises administering to the mammal an effective antiinflammatory or analgesic amount of a compound of claim 5.

20. A method of treating inflammation, pain or both in a mammal which comprises administering to the mammal an effective antiinflammatory or analgesic amount of a compound of claim 6.

21. A method of treating inflammation, pain or both in a mammal which comprises administering to the mammal an effective antiinflammatory or analgesic amount of a compound of claim 7.

* * * * *